United States Patent [19]

Boyd et al.

[11] 4,352,021
[45] Sep. 28, 1982

[54] X-RAY TRANSMISSION SCANNING SYSTEM AND METHOD AND ELECTRON BEAM X-RAY SCAN TUBE FOR USE THEREWITH

[75] Inventors: Douglas P. Boyd, Woodside; William B. Herrmannsfeldt, Los Altos; James R. Quinn, San Jose; Robert A. Sparks, Palo Alto, all of Calif.

[73] Assignee: The Regents of the University of California, Berkeley, Calif.

[21] Appl. No.: 109,877

[22] Filed: Jan. 7, 1980

[51] Int. Cl.³ .......................... A61B 6/00; H01J 35/00
[52] U.S. Cl. ...................................... 378/12; 378/146; 378/134
[58] Field of Search ....... 313/56; 250/445 T, 416 TV

[56] References Cited

U.S. PATENT DOCUMENTS

| | | | |
|---|---|---|---|
| 3,106,640 | 10/1963 | Oldendorf | 250/445 T |
| 3,852,605 | 12/1974 | Watanabe et al. | 250/401 |
| 4,045,672 | 8/1977 | Watanabe | 250/445 T |
| 4,075,489 | 2/1978 | Neal et al. | 250/402 |
| 4,144,457 | 3/1979 | Albert | 250/416 TV |
| 4,158,142 | 6/1979 | Haimson | 250/445 T |
| 4,199,684 | 4/1980 | Leunbach et al. | 250/445 T |
| 4,206,356 | 6/1980 | Wardley et al. | 250/445 T |
| 4,250,425 | 2/1981 | Gabbay et al. | 250/445 T |

Primary Examiner—Alfred E. Smith
Assistant Examiner—T. N. Grigsby
Attorney, Agent, or Firm—Flehr, Hohbach, Test, Albritton & Herbert

[57] ABSTRACT

A high speed multiple section, computed-tomographic x-ray scanner is provided. The scanner utilizes a multiple-anode, scanning electron beam x-ray source to provide high speed scanning of sections of the body. No mechanical motion is involved.

14 Claims, 13 Drawing Figures

FIG_1

FIG_2

FIG_3

FIG_4

FIG_5

FIG_6

FIG_7

FIG_8

FIG_9

FIG_11

FIG_10

FIG_12

FIG_13

X-RAY TRANSMISSION SCANNING SYSTEM AND METHOD AND ELECTRON BEAM X-RAY SCAN TUBE FOR USE THEREWITH

This invention relates generally to a high speed multiple section computed-tomographic (CT) x-ray transmission scanner and more particularly to a multiple target scanning-electron beam x-ray source providing rapid scan.

Presently available scanners use a mechanical scanning system of x-ray sources and detector arrays. In one typical design the x-ray source and detectors are moved in steps alternately in a transverse direction and by an angle (translate-rotate system). A faster scanning configuration uses only pure rotary motion of a fan x-ray source in combination with a stationary ring-shaped detector array. An alternative rotating system uses rotating detectors also, thus saving the number of detectors, see U.S. Pat. No. 4,075,492. The x-ray source is generally collimated so that a fan of pencil beams or continuous fan is generated with a fan angle in the 10° to 40° range. The x-ray source is then efficiently utilized to achieve simultaneous multiple fan ray scanning. Rotating systems are generally fastest but require about one second at best to obtain one section and 30 seconds at best to obtain a series of eight sections. Multiple sections covering a volume of interest are obtained by mechanical incrementation of the couch. This relatively slow scanning speed very seriously impairs the quality of medical x-ray diagnosis since biological rhythms and motions especially as heart beats are much faster, and obtainable image resolution of such objects are therefore marginal. Because of these limitations, special techniques have been developed to overcome some of the worst degradation in image quality of such objects.

One is to gate the scanning. The scanning is extended over a number of heart beats and is concentrated at phases where the heart muscles can come to a standstill in the reversal phase of their motion (systolic and diastolic phase of the cardiac cycle). Another useful method is to inject iodinated contrast fluids into the blood.

It is obvious, however, that full utilization of CT x-ray diagnosis, especially for heart diagnosis, can only be obtained with substantially faster scanning systems than those presently available and means for examining an entire volume, i.e., the heart, nearly simultaneously using multiple sections.

Two recent developments employ both electronic and mechanical scanning to improve the scanning speeds. One system incorporates lateral electronic scanning with a magnetically deflected electron beam. A single electron beam is deflected over a lateral target array and produces a corresponding lateral array of sequential x-ray sources. The second scanning direction is rotational and is accomplished mechanically. This system is more completely described in U.S. Pat. No. 4,045,672.

Although the resultant scanning speed of this system is not significantly faster than that of the best presently available mechanical scanners, it is significant in that it demonstrates the feasibility of electronic scanning methods using magnetic beam deflection. A magnetic beam deflection system is also described in U.S. Pat. No. 4,158,142 where there is described a method and apparatus for producing high intensity x-rays and directing such x-rays towards an object of interest from a fixed target by producing a high power electron beam, selectively directing the beam by means of selectively activated electromagnetic elements having no mechanically moving parts either to preselected points on the target for productions of x-ray therefrom or to an x-ray shielded beam collective position generally adjacent the target. The electron beam thus scans over the anode target producing x-rays which are collimated and directed through the body.

Another system presently being developed uses a semi-circular array of 28 individual x-ray tubes that are electronically switched on and off in succession. The electronic scanning speed for one section is very fast in the order of 10 milliseconds. This configuration provides a relatively poor resolution since the angular separation between adjacent x-ray sources is approximately 7°. In order to provide more accurate spatial resolution, the system is mechanically rotated. The system uses 28 vidicons and image intensifiers for detection.

The present invention is directed to an improved electronic scanning system which incorporates a single electron beam tube. The electron beam is rotated by a magnetic deflection system to produce a movable x-ray source on one of four adjacent semi-circular target rings to provide scanning fan beams that can be used to image an entire volume of tissue in multiple sections. Such an electronic scanning system is vastly superior in speed to the mechanical scanning systems described above. Fraction of a second scanning speed of a volume can be achieved as compared to one or more seconds required for the mechanical scan of a single section. The system eliminates the need for moving parts that require high precision and alignment. In addition, elaborate systems of sliding electrical contacts are eliminated. The present scanner is an improvement over that shown and described in U.S. Pat. No. 4,158,142 in that it permits nearly simultaneous viewing multiple sections of the body which may encompass a region as large as the heart. The scanner can provide as many as eight sections.

The present invention employs a plurality of detectors mounted opposite the target rings. The detectors are arranged in two adjacent semi-circular ring arrays. Each of the arrays contains a multiplicity of detectors as, for example, 210 detectors each, providing a total of 420 detectors. The angular separation of two adjacent detectors is in the order of 0.5 degrees resulting in very high resolution. The scanning system is provided with interchangeable collimators both for the x-ray source and for the detectors. The source collimator provides a fan-shaped beam that covers the body with a 30° opening angle. The detector collimators provide interchangeable options: dual section detector arrays, single section detector arrays and high resolution single section detector arrays. A variety of scanning modes can be selected with up to eight sections being scanned at a rate of at least one scan per second.

It is, therefore, a general object of the present invention to provide an improved x-ray transmission scanning system employing an electron beam scan tube.

It is another object of the present invention to provide an apparatus for obtaining x-ray absorption distribution of an object which includes an electron beam scan tube providing a plurality of adjacent movable x-ray sources together with a plurality of detectors mounted to receive the x-rays from said sources.

It is a further object of the present invention to provide an electron beam scan tube which includes a plurality of adjacent target rings and adjacent collimators to provide a plurality of adjacent fan beams together with a plurality of semi-circularly arranged detectors for receiving said fan beams and providing signals corresponding to the absorption characteristics of the object through which the x-rays are transmitted.

The foregoing and other objects are achieved by an x-ray transmission scanning system including an electron beam scan tube comprising an evacuated envelope having a longitudinal axis, said envelope including a cylindrical end portion and a semi-circular portion with an electron gun disposed axially of the cylindrical end portion and forming a highly collimated electron beam, focus coils disposed to receive and focus the beam, bending coils adapted to receive the beam and direct it into the semi-circular portion and scan it in a semi-circle, a plurality of adjacent semi-circular target rings disposed at the end of said semi-circular portion for receiving the electron beam and generating x-rays, a source collimator disposed adjacent each of said target rings to intercept said x-rays and provide a fan-shaped x-ray beam which rotates as the electron beam is moved along the target ring whereby to scan a plurality of adjacent sections one for each target ring.

Further, there is provided an apparatus for obtaining x-ray absorption distribution of an object including an electron gun of the foregoing type together with the semi-circular detector array including a plurality of detectors mounted into adjacent semi-circular ring arrays and detector collimators serving to direct the fan beams onto selected ones of said detectors.

The foregoing objects and invention will be more clearly understood from the following description in which the drawings are illustrative thereof.

Figure 1:
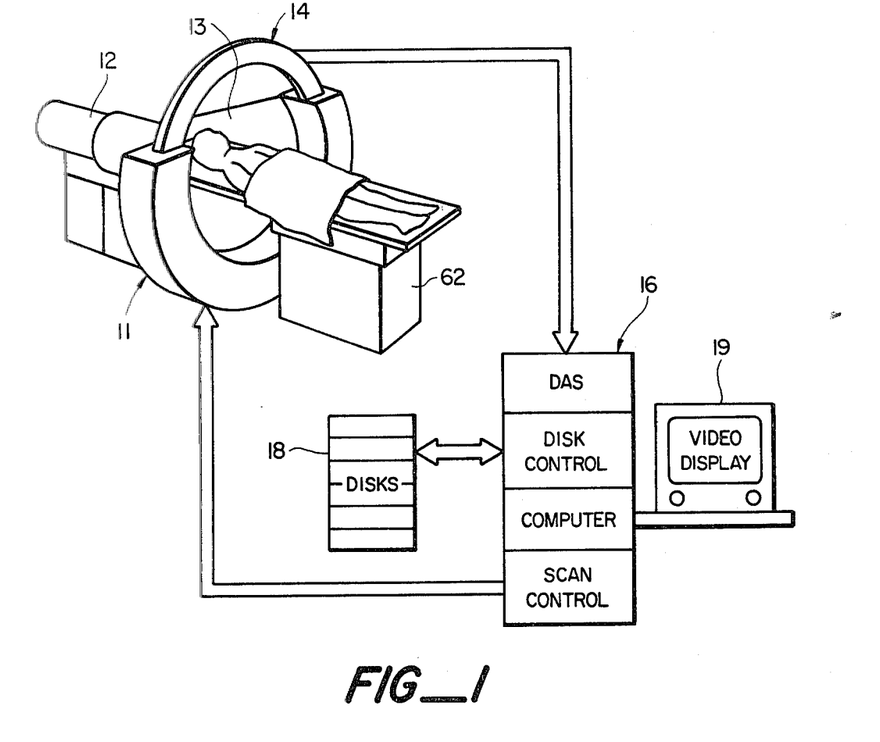
FIG. 1 is a schematic diagram partly in perspective showing a computed tomographic x-ray transmission scanning system in accordance with the invention.

Referring to FIG. 1, the system is seen to include three major components: a scan tube 11 including a cylindrical portion 12, and a semi-circular conical portion 13; a detectory array 14; and, a computer system 16. The scan tube projects an electron beam to target rings which generate x-rays. The x-rays are intercepted by the detector array 14. The output of the detector array is applied to the computer system 16. The computer system includes a plurality of storage discs 18 for recording the data for later processing. The computer system also includes an output which controls the scan tube. A video display 19 presents the data.

Figure 2:
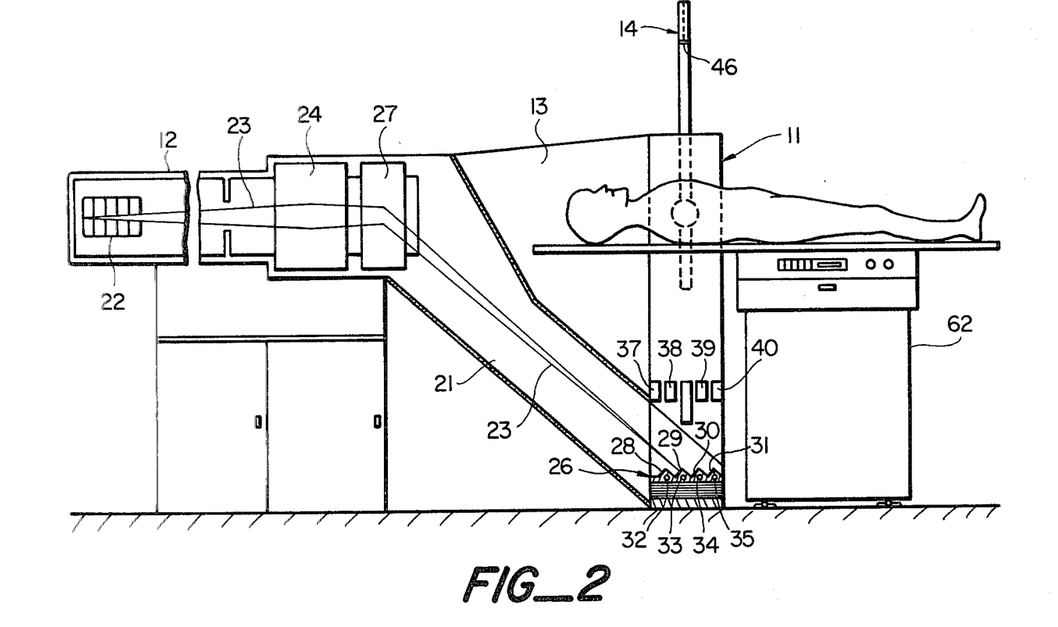
FIG. 2 is a cross sectional view of the system of FIG. 1.
Figure 3:
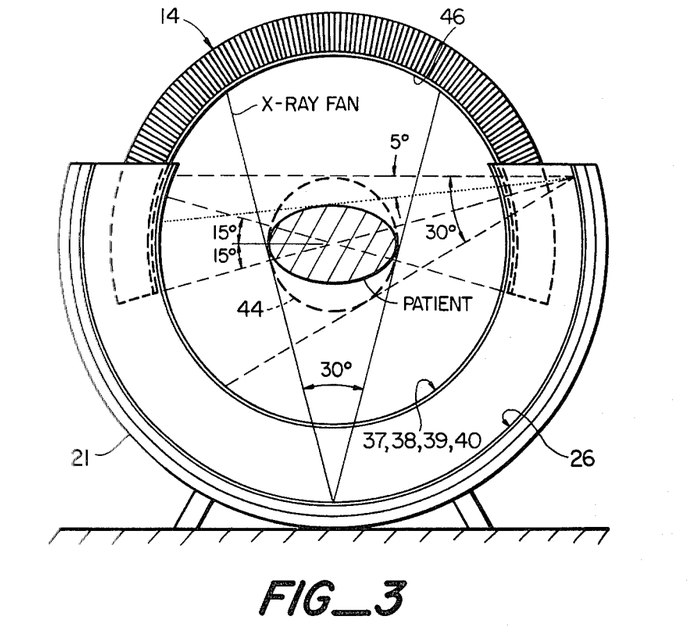
FIG. 3 is an end view of the system of FIG. 1.

Referring more particularly to FIGS. 2 and 3, the scanning system and detection system is shown in more detail. The electron beam tube 11 includes a vacuum envelope 21 which houses an electron gun 22 at the cylindrical end 12. The electron gun projects an axial electron beam 23 along the cylindrical portion. The focus coils 24 focus the beam onto targets 26. Bending coils 27 bend the beam so that it fans out along the semi-circular conical portion of the tube to impinge upon the semi-circular target rings. The target assembly 26 includes a plurality of semi-circular target rings 28, 29, 30 and 31. Suitable cooling coils 32, 33, 34 and 35 are associated with each of the target rings 28, 29, 30 and 31 respectively and serve to cool the target rings.

The bending magnets not only deflect the beam but rapidly sweep it along the semi-circular targets shown in FIGS. 2 and 3. The target rings are typically scanned serially to obtain a multiple section examination as will be presently described. Ring collimators 37, 38, 39 and 40 are disposed to intercept x-rays emitted by the target rings and define an x-ray beam projected as a one or two centimeter thick planar beam. An approximately 30° wide fan-shaped sector of this beam is detected by the curved detector array and utilized to reconstruct a tomographic image.

The detector array is in the form of a ring which overlaps the ring collimators. In the overlapping region the detector fits between the second and third collimator rings 38 and 39. The detector array 14 likewise may extend as much as 210° and is semi-circular. A suitable detector collimator 46 serves to pass the x-rays to the associated detector. As will be presently apparent, overlap of the source and detector rings assures that at least 180° of projection data can be obtained.

The reconstruction region is indicated by the dotted circle 44, FIG. 3, and has a radius of approximately 50 centimeters. For oval-shaped patients such as indicated by the shaded region, more than 190° of projection data can be obtained. The degree of overscanning increases to about 230° for posterior regions. Overscan is known to be an important feature of CT scanning that can be used to reduce streak artifacts due to data inconsistencies at 0° and 180°. This important principle is employed in the reconstruction software of the present system. The rays that pass outside the reconstruction circle are used to calibrate the individual detectors in the stationary array.

Figure 4:
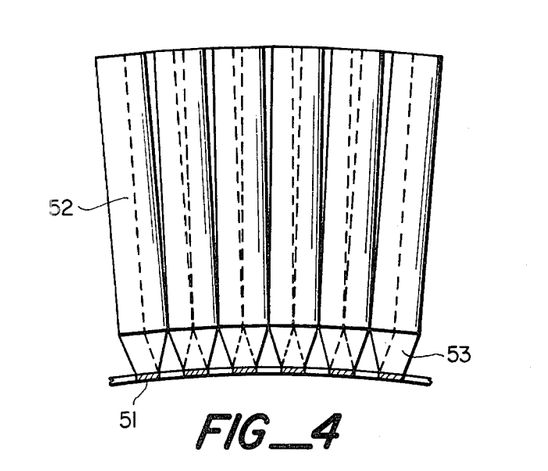
FIG. 4 is a side elevational view of a portion of the detector array.
Figure 5:
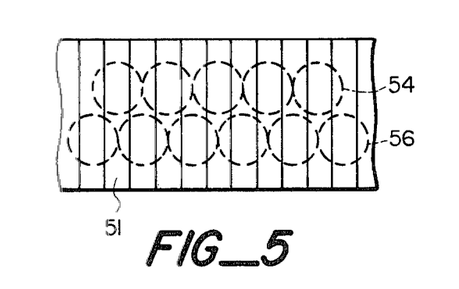
FIG. 5 is a front view of a portion of the detector array.
Figure 6:
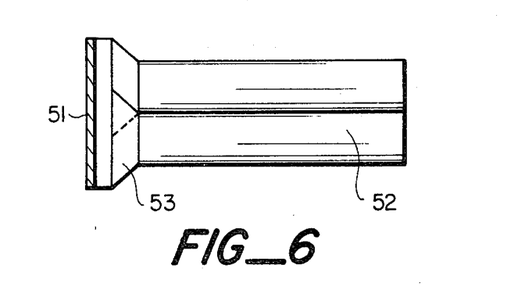
FIG. 6 is a side view of a portion of the detector array.

Referring more particularly to FIGS. 4, 5 and 6, the detector array 14 consists of a ring of bismuth germanate scintillator crystals 51 coupled to photomultipliers 52. Each scintillation crystal may, for example, be 7 millimeters by 40 millimeters. The assembly of scintillators is coupled by light pipes 53 to the photomultipliers 52. The assembly is shown including two rows of adjacent staggered photo tubes 54 and 56. In an alternative design, the photo tubes would be replaced by low-noise photodiodes. Since photodiodes and associated amplifiers are small and inexpensive, higher density arrays would be possible, leading to higher resolution images.

Figures 7, 8, 9, 10, 11:
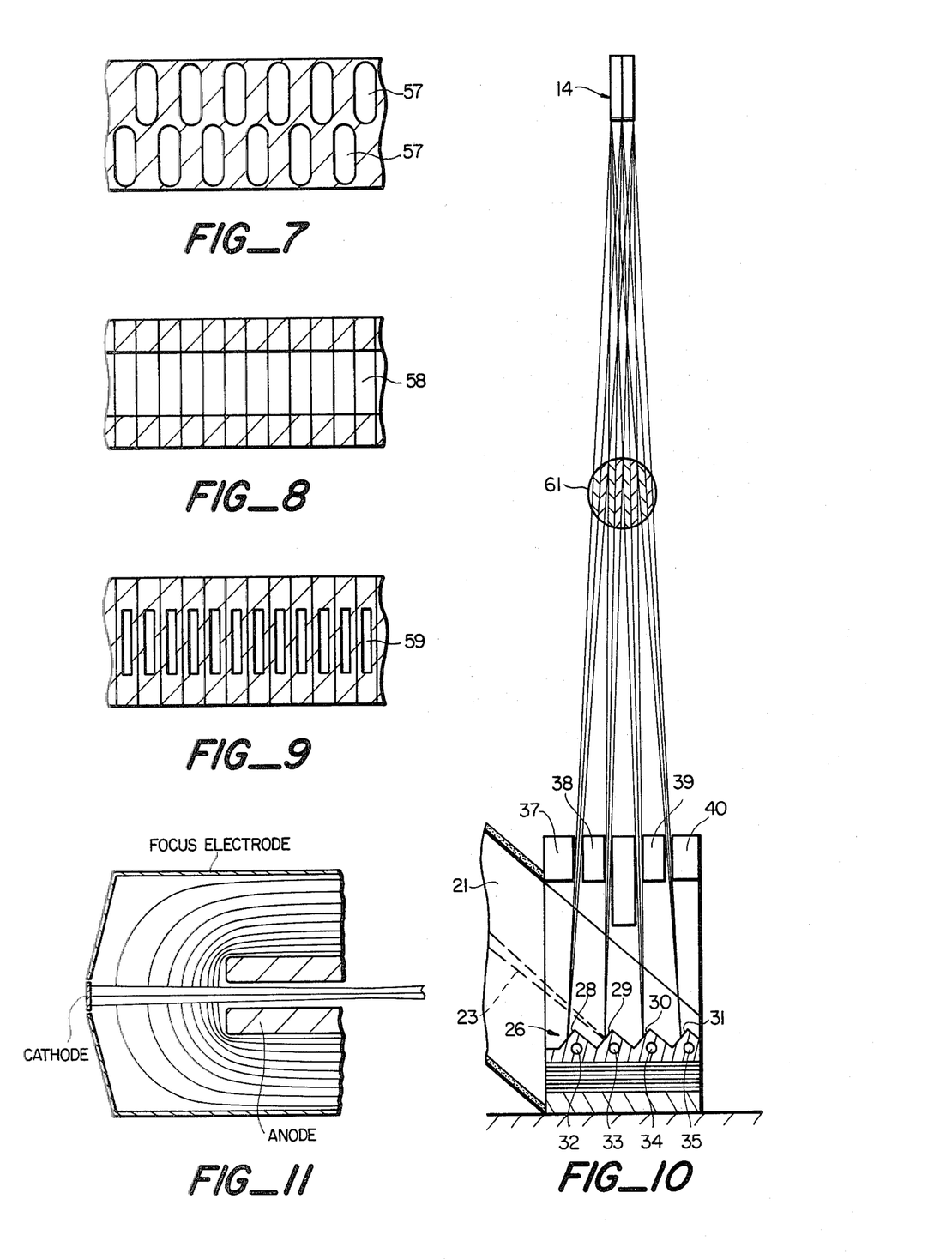
FIG. 7 shows a dual section collimator used in connection with the detector array.
FIG. 8 shows a single section collimator used in connection with the detector array.
FIG. 9 shows a high resolution collimator used in connection with the detector array.
FIG. 10 is an expanded cross sectional view showing of the target ring source collimators and illustrating the detectors.
FIG. 11 is a graph showing the electron gun design.

The x-rays from the targets are collimated by suitable masks which include a plurality of openings associated with each of the crystals. The collimator may include a plurality of staggered openings 57 as shown in FIG. 7, each of the openings being associated with an adjacent crystal and light pipe to transmit light along the associated light pipe 53 to the associated photo diode 52. Alternatively, the collimator may be a single section collimator including an opening which allows the x-ray beam to impinge upon the plurality of adjacent scintillator crystals with light transmitted to two light pipes. Finally, for high resolution, there may be provided a plurality of small openings 59 each associated with one of the crystals and with one of the light pipes.

The dual section collimator of FIG. 7 having openings 57 is used to define two rings of 210 detectors each. A single scan will thus produce a pair of side by side tomographic sections. The single section collimator having opening 58, FIG. 8, provides improved photon utilization in a single ring of 420 detectors for improved angular sampling. The high resolution collimator, FIG. 9, is a single section 420 element design with improved spatial resolution characteristics since each detector opening element 59 has a reduced width. The collimators are fabricated in a semi-circular ring 46 that can be quickly interchanged according to the planned mode of operation.

FIG. 10 shows the multiple section configuration obtained by serial scanning of the four target rings in combination with dual section detector collimators. For each target sweep, a pair of normally one centimeter thick sections are scanned. A collection of eight sections covers a region of approximately 10 centimeters indicated by the circle 61. This is sufficient to cover all of the left ventricle and most of the heart of a typical patient.

The tomographic sections will be slightly tilted, as illustrated, and the projection measurements will be only approximately isoplanar. However, dual section distortion is also used by other types of scanners and moderate amounts of aberrations are acceptable. Additional detector rings could be added to reduce the out-of-plane problem.

Referring again to FIG. 1, one sees the patient lying on a cantilevered couch inserted in the scanning circle. The couch is supported by a movable gurney 62 in order to vary the angle of the body axis with respect to the scanner axis. It will be possible to adjust the angular position to provide tomographic sections which are transverse to either the long or short axis of the heart.

Several modes of operation can be achieved by selecting a particular detector collimator and programming the data acquisition system. These modes will be used to optimize the configuration for particular application such as blood flow studies and high resolution studies.

The following are typical modes of operation. Mode A is used to determine regional myocardial perfusion and blood flow in coronary arteries and cavities. A basic scan speed of 50 milliseconds can be used for this mode to give an optimal combination of contrast and spatial resolution. A scan can be triggered by a physiological signal from the heart, for example, the electrocardiogram, so that the scans will occur during the diastolic phase of the heart cycle. Using four successive dual section scans, all eight sections of the heart will be scanned in 200 milliseconds. This sequence will be repeated on either successive beats or every other beat in order to allow the computer one full second for each sequence. Up to 16 eight section scans can be stored at the rate of one per second or slower. The exact phase of the cardiac cycle selected for scanning is not critical as long as the timing is repeatable from beat to beat. A 50 millisecond time scan is estimated to adequately freeze cardiac motion during the relatively slow expanding phase of diastole. However, if experience proves otherwise, an optional 25 millisecond mode can be selected. Analysis of sequential images will allow observation of the filling and washout of the intravenous bolus of contrast media in various regions of interest. A second mode of operation can be used to obtain cine-like images of a single transverse section at a frame rate of 40 per second, for a total of 32 images. In this mode a 25 millisecond scan speed can be used with a basic 42 microseconds sample speed. Thus, the distance this source travels per sample is extended from 3 to 6 millimeters and spatial resolution will be slightly degraded as compared to 50 microsecond scans to a line spread function of 3 millimeters. In addition, a small number of photons per scan lowers contrast resolution by the square root of 2. However, this small loss in resolution will be entirely adequate for motion study since the inner and outer edges of the myocardiam represent relatively high contrast structures and are easily defined to a fraction of the system spatial resolution. A 32 frame, motion study can be repeated for each of the other eight sections using successive beats as long as required if one sequence per second is not exceeded.

Mode C is reserved for ventricular volume studies and is used for computing ejection and ventricular performance. In this mode, dual sections can again be used to obtain scans at maximum diastole and minimum systole within a given heartbeat. The scans will be triggered by an appropriate physiological signal. This sequence will be repeated four times on successive beats in order to obtain volume studies for all sections of the heart. A 25 millisecond scan speed is used in order to facilitate stopping motion at varied peaks of the two cardiac phases.

The fourth mode, D, is used for high resolution studies. If stationary structures such as heart, abdomen or pelvis are scanned, dynamic studies with a basic exposure time of 400 milliseconds will be possible. A basic scan speed of 50 milliseconds will be used and 8 serial scans will be averaged. The special collimator with 3.5 millimeter openings will be used to achieve high spatial sharpness. If a high resolution study of the heart is needed, the eight averaged scans will be obtained on successive beats using gating. The basic purpose of this mode is to provide a capability for state of the art high image quality body scanning.

Referring now more particularly to the electron beam scan tube, the beam is generated by a diode gun having a dispenser cathode. Electron emission is controlled by space charge effects due to electrostatic fields. The beam is focused by a solenoid magnet 24 and bent through an angle of 33 to 40 degrees by rotating crossed dipole magnet 27. The electron beam is swept along the tungsten targets through an angle of rotation of 210°. The scan tube specifications are as follows:

Beam current 1000 mA
Acceleration potential: 120 kV
Electron gun: 6.3 mm diameter tungsten flat cathode, low convergence ratio modified Pierce diode.
Deflection angle: 33°–40°
Bend Magnet: 48 cm long by 58 cm diameter, magnetic field about 25 Oersted.
Focus coil: 40 cm long by 40 cm diameter, magnetic field about 40 Oersted.

Targets: Four tungsten ring targets at 33°, 34.5°, 35.7°, and 37°. All rings have a radius of 100 cm and range of 210°.

The electron beam is generated by a modified pierce diode gun. The dispenser cathodes consist of a tungsten disc with barium oxide dispersed throughout the cathode held at approximately 1,000° C. The electron emission is controlled by the space charge effect through the electrostatic field configuration represented by the equal potential lines, FIG. 11, and not by cathode temperature. After exiting the gun, the beam expands due to space charge effect and is refocused by the solenoid focusing coil 24. Before the refocused beam reaches a waist, a bending magnet 27 diverts the beam through a fixed angle. The sine wave time variation of the exciting voltages cause the plane of bend to rotate. At the beam waist, the beam strikes a tungsten annular ring to cause emission of x-rays. An x-ray opaque housing defines the fan beam geometry.

More particularly, the bending magnets 27 consist of two superimposed dipoles at 90° rotation. When powered by sine wave currents 90° out-of-phase, these magnets cause the beam to bend at a constant angle in a plane which is rotating at the frequency of the driving voltage. The dipoles are modified cosine-wound air core magnets. The magnetic field inside the magnet rotates, the magnet itself remains stationary. Since the device is iron-free, the upper frequency cutoff is about 1 KHZ and scan times of 0.001 seconds are possible. The angle of bend is determined by the amplitude of the applied sine wave current, changes in bend angle cause target switching.

The entire envelope 21 is stainless steel, the magnets are outside the envelope for reasons of maintainability. A magnetic shield will encase the entire device and protect the beam optic system from stray magnetic fields generated from nearby equipment. The vacuum is maintained by an external pumping source. Electron beam intensity is preferably monitored during the scan. Electrical monitoring of cathode current and anode current may provide adequate intensity monitoring. If not, an additional scintillating detector is placed near the target in order to monitor scattered x-ray intensity. This scintillator will be of a fast plastic type shaped into a 210° arc of radius of 90 cm and placed inside the source collimator housing. Signals from the scintillator are digitized and recorded along with the data from the detector ray during the scan. After calibration, the monitor data will be used to normalize the projected data.

The spot position on the target is determined by recording the high voltage and bending magnet excitation currents. Since the magnets are air core, these values uniquely determine the position of the beam spot and are recorded during the scan similar to the procedure for intensity monitoring. An auxiliary system of secondary emission beam position monitors is included for calibration purposes and as a backup system for redundancy. The secondary emission monitors consist of a series of thin wires crossed perpendicular to the target and a few millimeters above the surface within the vacuum. These wires will have a positive voltage applied in order to collect the electrons emitted from the target. The output current of each wire is a function of time, will be proportional to the profile of the scanning electron beam. The width of this profile will indicate spot size and its peak position and will indicate the exact time of arrival of the beam at the location of the wire.

The scan control computer is programmed to provide safety interlocks to protect the scan tube and the patient from any unusual condition in beam position or intensity. The beam can be shut down in one millisecond after receiving an abort instruction from the computer.

The x-ray tube, as described, has four separate x-ray producing targets each consisting of a 210° tungsten arc with a radius of 1 meter. The electron beam sweeps the length of the target in 25 milliseconds or 50 milliseconds and has a cross section at the level of the anode of about 2.5 millimeters by 5 millimeters. The target angle is 10°, resulting in an effective focal spot having a size of 2.5 millimeters by 1 millimeter. At 120 KV and 1,000 amps the power applied to the target is 120 KW.

The electron gun design was obtained by using an electron optics computer program. A view of the graphics output of this program is shown in FIG. 11 which shows the beam and the electrostatic fields adjacent to the cathode and throughout the length of the tube.

Figure 12:
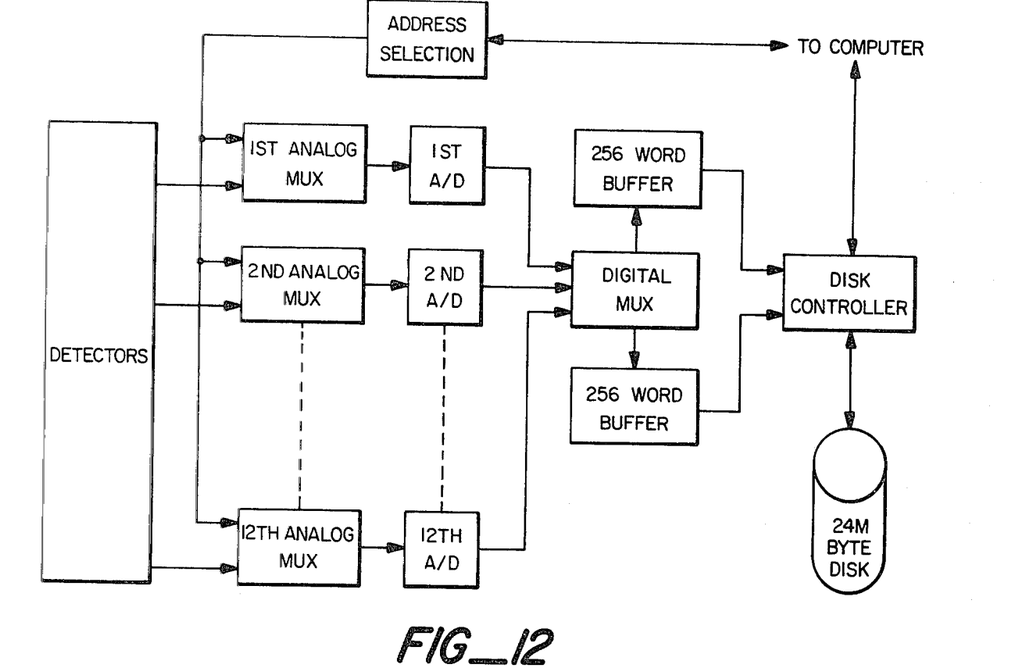
FIG. 12 is a block diagram of a data acquisition module suitable for use in the scanning system of the present invention.
Figure 13:
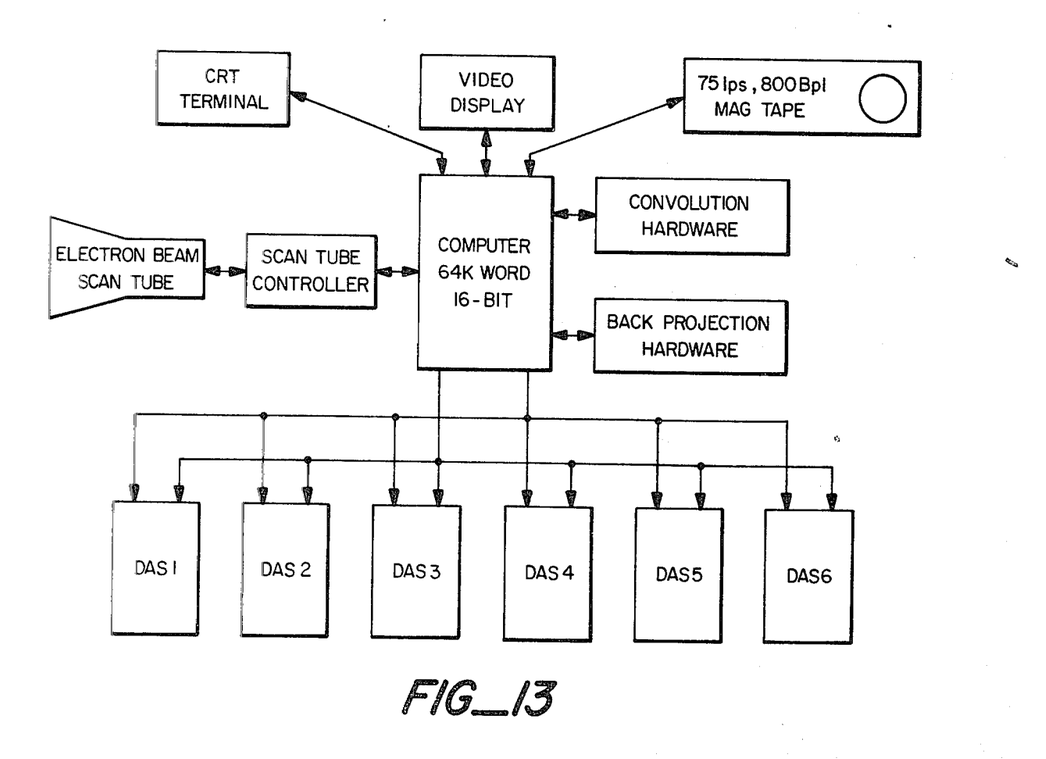
FIG. 13 is a block diagram of a data acquisition and reconstruction system suitable for use in the scanning system of the present invention.

Each detector will have a log amplifier and two integrators. FIG. 12 is a detailed diagram of a data acquisition module and FIG. 13 is a block diagram of the data processing system. As previously explained, the detectors are arranged in an arc of 210° about the center of reconstruction. The detectors are numbered in the order that they appear in the arc, from 1 to 420. Odd numbered detectors are in one plane, even numbered detectors are in the second plane. Detectors numbered 1 and 2 are at zero degrees, detectors numbers 419 and 420 are at 210°. The data from the detectors is recorded on disc in data acquisition systems DAS. DAS 1 collects data from detectors numbered 1, 7, 13, 29 etc. DAS 2 collects data from detectors 2, 8, 14, 20 etc. DAS 3 collects data from detectors 3, 9, 15 etc. DAS 4 collects data from detector numbers 4, 10, 16, 22 etc. DAS 5 collects data from detectors 5, 11, 17, 23 etc. DAS 6 collects data from detector numbers 6, 12, 18, 24, etc. The x-ray fan angle originating at the anode is 30° which therefore covers 70° in the detector ring. Thus, only 140 detectors will be in the fan at any time or at most 24 for any given disc. The data acquisition system is of the form shown in FIG. 13. The disc in each system has associated with it 12 analog-to-digital convertors 71. Each analog-to-digital convertor (A/D) 71 has an analog multiplexer which is attached to 6 detectors. For disc number 1, A/D 1 is attached to detectors 173, 145, 217; A/D 2 is attached to detectors 7, 79, 151, 223, 295, 367; and A/D 12 is connected to detectors 67, 139, 211, 283, 355. The total collection time for a given scan is 0.05 seconds. During each sample interval at most 140 detectors are read. Each analog-to-digital convertor must digitize two detectors during a given sample interval. During data collection the discs are written continuously. Sectors of 256 words are written alternately in one buffer and then the other. Since disc writing is somewhat faster than the data collection, the buffer will never be quite full. Therefore, a special word is written after the collected data in each 256 bit sector.

On each disc four tracks can be written without moving the read-write heads. On the fifth revolution the heads must be moved so during this time the data is written onto one of the fixed head tracks. At the start of the sixth revolution the moving heads will have settled. Therefore, 1/5 of the data is written with the fixed head and 4/5 with the moving heads. The disc rotates 60 times per second. In the worst case data is collected continuously for 0.8 seconds or 48 disc revolutions, data is written with moving heads during 39 revolutions with fixed heads during 9. In this case only one plane of 210 detectors are being read and, therefore, only three discs are collecting data. At the end of the 0.8 second period there is time to move the data from fixed head tracks to the other three discs. Six discs can hold all the data for a given study.

The computer is used to select the detectors to be sampled during each sample period, to control the scan tube, to control the disc and the magnetic tape driven and to process the data. To process the data for a given slice, a standard convolution back projection algorithm is used. First, the data is read from the disc into the computer and recorded and rebinned into 420 parallel beam profiles each with about 267 data panels. This data will represent one or two sections, depending on the collimator option. Special convolution and back projection hardware is used to reconstruct a 160 by 160 matrix in less than 60 seconds for each section. A study with 128 slices would take about two hours to process if the entire picture is to be reconstructed for each section. Typically, only a partial reconstruction of 128 by 128 region encompassing the heart will be needed. In this case, reconstruction of a complete study requires less than one hour.

The software for the computer includes four parts-data acquisition, preprocessing, image reconstruction and image display. Data acquisition software controls the electron bean scan, controls the data acquisition system and writes data onto disc files as described above. The data preprocessing adjusts for the gain and offset of each photomultiplier tube and normalizes for the x-ray intensity during each sample. The intensity data is then linearized. Image reconstruction includes reordering and rebinning. A separate algorithm will be needed for the 25 and 50 millisecond modes. Reconstruction involves convolution in the spatial domain followed by back projection. The data is then processed for display.

What is claimed is:

1. In an x-ray transmission scanning system an electron beam scan tube for providing a plurality of adjacent movable x-ray sources comprising:
    an evacuated envelope having a longitudinal axis;
    an electron gun disposed axially at one end of the envelope projecting an electron beam along said axis;
    a focus coil spaced from said gun to receive and focus said beam;
    a plurality of adjacent longitudinally spaced curvilinear elongated targets disposed at the other end of said envelope to receive the electron beam and generate x-rays in response thereto;
    means for moving said focused electron beam along said targets and from one target to another; and
    a source collimator having an elongated slot disposed adjacent to each of said elongated targets to intercept said x-rays and provide an x-ray beam which fans outwardly from the received electron beam to form a fan shaped beam which rotates as the electron beam is moved along the corresponding target whereby to scan a plurality of adjacent longitudinally spaced sections at least one for for each of said targets.

2. An x-ray transmission scanning system as in claim 1 wherein said target and collimator slots lie on circles having their centers on said longitudinal axis.

3. An apparatus for obtaining an x-ray absorption distribution of an object comprising:
    an evacuated elongated envelope having a longitudinal axis;
    an electron gun disposed axially at one end of said envelope and projecting an electron beam along said axis;
    a focus coil spaced from said gun to receive and focus said beam;
    a plurality of adjacent longitudinally spaced curvilinear elongated targets disposed at the other end of said envelope to receive said electron beam and generate x-rays in response thereto;
    means for moving said focused beam and direct it to a selected one of said targets and scan the beam along said target;
    a source colliminator having an elongated slot adjacent to each of said elongated targets to intercept said x-rays and form an x-ray beam which fans outwardly from the received electron beam to form a fan shaped beam which rotates as the electron beam is moved along the corresponding target whereby to scan a plurality of adjacent longitudinally spaced sections, at least one for each target;
    a plurality of detectors mounted opposite the elongated targets, said detectors arranged to form an elongated array, and
    detector collimators serving to direct the beam onto selected ones of said detectors for each target.

4. In an x-ray transmission scanning system an electron beam scan tube for providing a plurality of adjacent movable x-ray sources comprising:
    an evacuated envelope having a longitudinal axis, said envelope including a cylindrical end portion and a semi-circular conical portion;
    an electron gun disposed axially at the cylindrical end and projecting an electron beam;
    a focus coil spaced from the electron gun disposed at the cylindrical portion to receive and focus said beam;
    bending coils spaced from said electron gun at the cylindrical portion adapted to receive said beam and direct it into said conical portion and scan the beam along selected target rings along a path which lies on a line;
    a plurality of adjacent target rings disposed at the end of said conical section to receive the electron beam and generate x-rays in response thereto; and
    a source collimator disposed adjacent each of said target rings to intercept said x-rays and provide a fan-shaped x-ray beam which rotates as the electron beam is moved along the corresponding target ring whereby to scan a plurality of adjacent sections one for each of said target rings.

5. An apparatus for obtaining an x-ray absorption distribution of an object comprising:
    an evacuated envelope having a longitudinal axis, said envelope including a cylindrical end portion and a conical semi-circular end portion;
    an electron gun disposed axially at the cylindrical end and projecting an electron beam;
    a focus coil disposed at the cylindrical portion to receive and focus said beam;
    bending coils following the focusing coil adapted to receive said beam and direct it into the conical end section and scan the beam along the segment of a circle;

a plurality of adjacent target rings disposed at the end of said conical section to receive said electron beam and generate x-rays in response thereto;

a source collimator adjacent each of said target rings to intercept said x-ray and form a fan-shaped x-ray beam which rotates as the electron beam is moved along the corresponding target ring whereby to form a plurality of fan-shaped x-ray beams to scan a plurality of adjacent sections, at least one for each target ring; and a plurality of detectors mounted opposite the target ring, said detectors arranged to form an array which is a segment of a circle; and detector collimators serving to direct the beam onto selected ones of said detectors for each target ring.

6. Apparatus as in claim 5 in which said source collimators are on a segment of a circle and in which said source and detector collimators overlap.

7. Apparatus as in claim 5 wherein said source collimators and detector collimators are arranged so that a single sweep of a target ring provides multiple scans.

8. Apparatus as in claim 5 wherein said source collimators and detector collimators are arranged so that with each sweep of the plurality of target rings there is scanned at least twice as many sections.

9. Apparatus as in claim 5 in which including means for receiving the output of said detectors, processing the output and recording the processed signals.

10. Apparatus as in claim 9 including means for receiving said processed detector signals and reconstructing an image of scanned sections.

11. Apparatus as in claim 7 including means for controlling the electron beam scan.

12. Apparatus as in claim 9 including means for displaying the reconstructed image.

13. In an x-ray transmission scanning system an electron beam scan tube for providing a plurality of adjacent movable fan-beam x-ray sources comprising an elongated evacuated envelope having a longitudinal axis, an electron gun disposed axially at one end of said evacuated envelope serving to project an electron beam along the axis of the evacuated envelope, a focus coil spaced from said gun surrounding said evacuated envelope and adapted to form magnetic fields which focus the beam, a plurality of adjacent elongated targets each lying on a circle having its center at said axis and spaced at different distances from said electron gun disposed at the other end of said envelope to receive said electron beam and generate x-rays, means for sequentially scanning said beam along each of said elongated targets, a source collimator lying on a circle having its center at said axis and including a slot disposed adjacent each of said targets to interrupt the x-rays from each target and pass x-rays through said slot to provide a fan shaped x-ray beam from each of said targets which x-ray beam rotates as the electron beam travels along each of the targets, said targets and collimators serving to form longitudinally spaced rotating fan beams, one for each of said targets and associated collimator slot.

14. Apparatus as in claim 13 wherein said electron deflection means comprises a beam bending coil spaced from said electron gun encircling said elongated envelope.

* * * * *

UNITED STATES PATENT AND TRADEMARK OFFICE
CERTIFICATE OF CORRECTION

PATENT NO. : 4,352,021

DATED : September 28, 1982

INVENTOR(S) : Douglas P. Boyd et al

It is certified that error appears in the above—identified patent and that said Letters Patent is hereby corrected as shown below:

Column 1, Line 5 add:

This invention was made with Government support under Grant No. 1 R01 HL-23430-01A1 awarded by the National Heart, Lung, and Blood Institute. The Government has certain rights in this invention.

Signed and Sealed this

Ninth Day of August 1983

[SEAL]

Attest:

Attesting Officer

GERALD J. MOSSINGHOFF

Commissioner of Patents and Trademarks